United States Patent [19]

Nakano et al.

[11] Patent Number: 5,399,695
[45] Date of Patent: Mar. 21, 1995

[54] METHOD FOR THE SYNTHESIS OF QUATERNARY AMMONIUM SALTS

[75] Inventors: Shinji Nakano, Takatsuki; Takao Morimoto, Katano; Takeshi Endo, Yokohama, all of Japan

[73] Assignee: Nippon Paint Co., Ltd., Osaka, Japan

[21] Appl. No.: 45,531

[22] Filed: Apr. 9, 1993

[30] Foreign Application Priority Data

Apr. 10, 1992 [JP] Japan .................................. 4-117928

[51] Int. Cl.⁶ ..................... C07C 211/27; C07F 9/92
[52] U.S. Cl. .......................................... 546/9; 546/10; 564/282
[58] Field of Search ...................... 546/9, 10; 564/282

[56] References Cited

PUBLICATIONS

Chemical Abstracts, vol. 115(17) Abst. No. 115:184,581-n, Oct. 28, 1991.

*Primary Examiner*—Alan L. Rotman
*Attorney, Agent, or Firm*—Millen, White, Zelano & Branigan

[57] ABSTRACT

Provided is a convenient method for synthesizing quaternary ammonium salts which are useful as curing catalysts for one-part thermosetting resin compositions which maintain storage stability at room temperature. The ammonium salts are synthesized by direct reaction of a benzyl alcohol or a benzyl alkyl ether optionally having on the benzene ring and/or at α-position one or more substituent groups inert to the intended reaction, with a corresponding strong-acid salt of a tertiary amine.

11 Claims, No Drawings

METHOD FOR THE SYNTHESIS OF QUATERNARY AMMONIUM SALTS

BACKGROUND OF THE INVENTION

There have been disclosed quaternary ammonium salts which can undergo thermal cleavage to yield acids in our U.S. Pat. Nos. 5,066,722 and 5,070,161. These compounds are useful as curing catalysts for one-part thermosetting resin compositions which are stable during storage at room temperature.

In the above cited patent literature, these compounds have been synthesized through two reaction processes: (a) According to a conventional method for the synthesis of quaternary ammonium salts, an amine corresponding to the final product is first subjected to the reaction with a corresponding benzyl halide (i.e. a quaternizing agent) to obtain a quaternary ammonium halide. (b) Then, the halide anion of thus obtained quaternary ammonium halide are replaced with a desired anion.

SUMMARY OF THE INVENTION

The present inventors searched for a convenient method for the synthesis of these compounds, and, as a result, succeeded in directly synthesizing desired quaternary ammonium salts by subjecting a strong-acid salt of a tertiary amine intended to be quaternized and a corresponding benzyl alcohol or a benzyl alkyl ether (the alkyl group being a C1-C4 saturated hydrocarbon group) to a dehydration condensation reaction.

It therefore is the object of the present invention to provide a convenient method for synthesizing a quaternary ammonium salt. More specifically, it is the object of the present invention to provide a method for synthesizing a quaternary ammonium salt, characterized in that a benzyl alcohol or a benzyl alkyl ether (the alkyl group being a C1-C4 saturated hydrocarbon group) optionally having on the benzene ring and/or at α-position one or more substituent groups inert to the intended reaction is allowed to react with a strong-acid salt of a tertiary amine. The reaction is optionally carried out in the presence of an excess tertiary amine on molar basis up to 9 times relative to said strong-acid.

DETAILED DISCUSSION

Among benzyl alcohols or benzyl alkyl ethers which can be used in the present method for the synthesis, the alcohols or ethers of the formula:

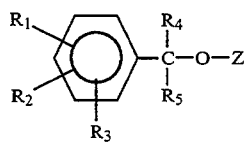

wherein $R_1$, $R_2$ and $R_3$ independently of one another denote hydrogen, hydroxyl, halogen, alkyl, alkoxy, nitro, amino, alkylamino, acyl, cyano, alkoxycarbonyl or carbamoyl, $R_4$ and $R_5$ independently of one another denote hydrogen, halogen or alkyl, and Z denotes hydrogen or a C1-C4 saturated hydrocarbon group, are preferred.

Among tertiary amines, the pyridine of the formula:

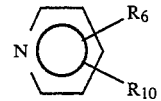

wherein $R_6$ and $R_{10}$ independently of one another denote hydrogen, hydroxyl, halogen, alkyl, alkoxy, nitro, amino, alkylamino, acyl, cyano, alkoxycarbonyl or carbamoyl, or the aniline derivatives of the formula:

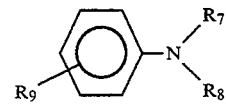

wherein $R_7$ and $R_8$ independently of one another denote alkyl or alkenyl, and $R_9$ denotes hydrogen, hydroxyl, halogen, alkyl, alkoxy, nitro, amino, alkylamino, acyl, cyano, alkoxycarbonyl or carbamoyl, are preferred.

Among strong acid which form salts with tertiary amines, $HAsF_6$, $HSbF_6$, $HBF_4$, $HPF_6$, $HClO_4$, $HFeCl_4$, $HCF_3SO_3$ or an aromatic sulfonic acid are preferred.

The synthesis is attainable by subjecting a corresponding strong-acid salt of a tertiary amine to the reaction with a corresponding benzyl alcohol or benzyl alkyl ether in an aprotic solvent such as benzene, toluene, ethyl acetate, butyl acetate, acetone, methyl isobutyl ketone, dichloromethane, dichloroethane, tetrahydrofuran, dioxane, nitromethane, nitrobenzene, acetonitrile and the like, at 0° C. to the boiling temperature of the solvent. The synthesis is also attainable in the presence of added tertiary amine (base) which has lower basisity than that of the base component of the strong-acid salt used. Thus, such a tertiary amine (base) can optionally be added to the reaction mixture in an amount on molar basis up to 9 times of the strong-acid salt used in the synthesis.

In order to remove water generated as a by-product, a small amount of dehydrating agents such as magnesium sulfate, sodium sulfate, a molecular sieve and the like can be added to the reaction mixture.

EXAMPLES

Example 1

Synthesis of N-benzylpyridinium hexafluoroantimonate 10.81 g (0.1 mol) of benzyl alcohol and 31.58 g (0.1 mol) of pyridine hexafluoroantimonate were dissolved in 80 g of acetonitrile and allowed to react at 80° C. for 8 hours. After the completion of the reaction, the mixture was concentrated, and the precipitated white solid was washed with ether and dried to give N-benzylpyridinium hexafluoroantimonate. Yield: 40%.

Example 2

Synthesis of N-α, α-dimethylbenzylpyridinium hexafluoroantimonate 13.6 g (0.1 mol) of 2-phenyl-2-propanol and 31.58 g (0.1 mol) of pyridine hexafluoroantimonate were dissolved in 60 g of methyl ethyl ketone and allowed to react at 60° C. for 6 hours. After completion of the reaction, the mixture was concentrated, and the precipitated white solid was washed with ether and dried to give the titled compound. Yield: 30%.

Example 3

Synthesis of N-(4-methylbenzyl)-N,N-dimethylanilinium hexafluoroantimonate 12.21 g (0.1 mol) of 4-methylbenzylalcohol and 35.78 g (0.1 mol) of N,N-dimethylaniline hexafluoroantimonate were dissolved in 100 g of nitromethane and allowed to react at 80° C. for 8 hours. After the completion of the reaction, the mixture was concentrated, and the precipitated white solid was washed with ether and dried to give the titled compound. Yield: 55%.

Example 4

Synthesis of N-(4-methoxybenzyl)-N,N-dimethylanilinium hexafluorantimonate 13.81 g (0.1 mol) of 4-methoxybenzylalcohol and 35.78 g (0.1 mol) of N,N-dimethylaniline hexafluoroantimonate were dissolved in 100 g of nitromethane and, after the addition of 12.04 g (0.1 mol) of magnesium sulfate, allowed to react at 80° C. for 4 hours. After the completion of the reaction, the mixture was filtered and the filtrate was concentrated. The precipitated white solid was washed with ether and dried to give the titled compound. Yield: 70%.

Example 5

Synthesis of N-$\alpha$, $\alpha$-dimethylbenzylpyridinium hexafluoroantimonate 75.0 g (0.5 mol) of $\alpha$, $\alpha$-dimethylbenzyl methyl ether and 31.58 g (0.1 mol) of pyridinium hexafluoroantimonate were dissolved in 200 g of dichloroethane and allowed to react at 70° C. for 4 hours. After the completion of the reaction, the mixture was concentrated, and the precipitated white solid was washed with ether and dried to give the titled compound. Yield: 67%.

Example 6

Synthesis of N-$\alpha$, $\alpha$-dimethylbenzylpyridinium hexafluoroantimonate 68.0 g (0.5 mol) of $\alpha$, $\alpha$-dimethylbenzylalcohol and 31.58 g (0.1 mol) of pyridinium hexafluoroantimonate were dissolved in 200 g of dichloroethane and allowed to react at 70° C. for 7 hours. After the completion of the reaction, the mixture was concentrated, and the precipitated white solid was washed with ether and dried to give the titled compound. Yield: 83%.

Example 7

Synthesis of N-$\alpha$, $\alpha$-dimethylbenzylpyridinium hexafluoroantimonate 68.0 g (0.5 mol) of $\alpha$, $\alpha$-dimethylbenzylalcohol, 31.58 g (0.1 mol) of pyridinium hexafluoroantimonate and 1.58 g (0.02 mol) of pyridine were dissolved in 200 g of dichloroethane and allowed to react at 70° C. for 10 hours. After the completion of the reaction, the mixture was concentrated, and the precipitated white solid was washed with ether and dried to give the titled compound. Yield: 79%.

Example 8

Synthesis of N-$\alpha$, $\alpha$-dimethylbenzylpyridinium hexafluoroantimonate 68.0 g (0.5 mol) of $\alpha$, $\alpha$-dimethylbenzylalcohol, 31.58 g (0.1 mol) of pyridinium hexafluoroantimonate and 2.08 g (0.02 mol) of 2-cyanopyridine were dissolved in 200 g of dichloroethane and allowed to react at 70° C. for 4 hours. After the completion of the reaction, the mixture was concentrated, and the precipitated white solid was washed with ether and dried to give the titled compound. Yield: 56%.

What is claimed is:

1. A method for synthesizing a quaternary ammonium salt comprising reacting, under effective conditions, a strong-acid salt of a tertiary amine with a benzyl alcohol or a benzyl alkyl ether in which the alkyl group is a $C_1$-$C_4$ saturated hydrocarbon group, optionally having on the benzene ring, at $\alpha$-position or both, one or more substituent groups inert to the intended reaction and recovering said quaternary ammonium salt from the reaction mixture.

2. A method for the synthesis according to claim 1, wherein said benzyl alcohol or benzyl alkyl ether has the formula:

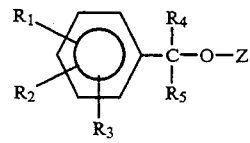

wherein $R_1$, $R_2$ and $R_3$ independently of one another denote hydrogen, hydroxyl, halogen, alkyl, alkoxy, nitro, amino, alkylamino, acyl, cyano, alkoxycarbonyl or carbamoyl, $R_4$ and $R_5$ independently of one another denote hydrogen, halogen or alkyl, and Z denotes hydrogen or a C1-C4 saturated hydrocarbon group.

3. A method according to claim 1, wherein said tertiary amine is a pyridine of the formula:

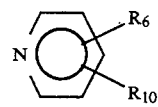

wherein $R_6$ and $R_{10}$ independently of one another denote hydrogen, hydroxyl, halogen, alkyl, alkoxy, nitro, amino, alkylamino, acyl, cyano, alkoxycarbonyl or carbamoyl.

4. A method according to claim 1, wherein said tertiary amine is an aniline derivative of the formula:

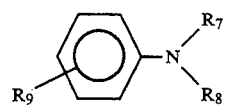

wherein $R_7$ and $R_8$ independently of one another denote alkyl or alkenyl, and $R_9$ denotes hydrogen, hydroxyl, halogen, alkyl, alkoxy, nitro, amino, alkylamino, acyl, cyano, alkoxycarbonyl or carbamoyl.

5. A method according to claim 1, wherein said strong acid is $HAsF_6$, $HSbF_6$, $HBF_4$, $HPF_6$, $HClO_4$, $HFeCl_4$, $HCF_3SO_3$ or an aromatic sulfonic acid.

6. A method according to claim 1, wherein the reaction is carried out in the presence of an excess of a tertiary amine on molar basis up to 9 times relative to said strong-acid.

7. A method according to claim 1, wherein said reaction is conducted in an aprotic solvent.

8. A method for synthesizing an N-benzylpyridinium salt which comprises reacting a benzyl alcohol of the formula:

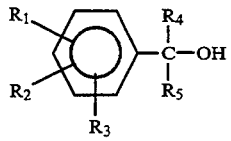

wherein $R_1$, $R_2$ and $R_3$, independently of one another, denote hydrogen, halogen, alkyl, alkoxy, nitro, acyl, cyano or alkoxycarbonyl and $R_4$ and $R_5$ independently of one another denote hydrogen, halogen or alkyl, or a $C_1$–$C_4$ alkyl ether of said benzyl alcohol,
with an acid addition salt of $HAsF_6$, $HSbF_6$, $HBF_4$, $HPF_6$ or $HCF_3SO_4$ and a pyridine of the formula

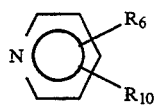

wherein $R_6$ and $R_{10}$ independently of one another denote hydrogen, halogen, alkyl, alkoxy, nitro, acyl, cyano or alkoxycarbonyl,
in an aprotic solvent under conditions effective to quaternize said pyridine salt with said benzyl alcohol or alkyl ether thereof.

9. The method according to claim 8, wherein the reaction is carried out in the presence of the base form of said pyridine or a tertiary amine having a basicity lower than the basicity of said base form of the pyridine.

10. A method for synthesizing an N-benzylanilinium salt which comprises reacting a benzyl alcohol of the formula:

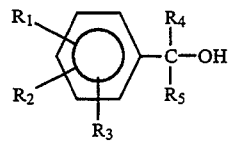

wherein $R_1$, $R_2$ and $R_3$, independently of one another, denote hydrogen, halogen, alkyl, alkoxy, nitro, acyl, cyano or alkoxycarbonyl and $R_4$ and $R_5$ independently of one another denote hydrogen, halogen or alkyl, or a $C_1$–$C_4$ alkyl ether of said benzyl alcohol,
with an acid addition salt of $HAsF_6$, $HSbF_6$, $HBF_4$, $HPF_6$ or $HCF_3SO_4$ and an aniline derivative of the formula

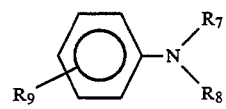

wherein $R_7$ and $R_8$ independently of one another denote alkyl or alkenyl, and $R_9$ denotes hydrogen, halogen, alkyl, alkoxy, nitro, acyl, cyano or alkoxycarbonyl,
in an aprotic solvent under conditions effective to quaternize said pyridine salt with said benzyl alcohol or alkyl ether thereof.

11. The method according to claim 10, wherein the reaction is carried out in the presence of the base form of said aniline derivative or a tertiary amine having a basicity lower than the basicity of said base form of the aniline.

* * * * *